United States Patent [19]

Wiesner

[11] Patent Number: 4,834,901

[45] Date of Patent: May 30, 1989

[54] SKUNK ODOR SHAMPOO

[75] Inventor: Charles J. Wiesner, P.O. Box 3479, Station B, Fredericton, N.B., Canada, E3A 5H2

[73] Assignee: Charles J. Wiesner, Fredericton, Canada

[21] Appl. No.: 111,419

[22] Filed: Oct. 22, 1987

[30] Foreign Application Priority Data

Mar. 17, 1987 [CA] Canada .................................. 532262

[51] Int. Cl.⁴ .......................... A61K 7/32; A61K 7/50; A61L 9/01; C11D 3/395

[52] U.S. Cl. ................... 252/95; 252/187.2; 252/187.24; 252/DIG. 5; 252/DIG. 13; 422/5; 424/70; 424/76.1

[58] Field of Search .......... 252/95, DIG. 5, DIG. 13, 252/186.42, 187.2, 187.24; 424/70, 76; 422/5

[56] References Cited

U.S. PATENT DOCUMENTS

| 2,683,074 | 7/1954 | Kuehner | 21/53 |
|---|---|---|---|
| 3,049,399 | 8/1962 | Gamson et al. | 21/53 |
| 3,843,781 | 10/1974 | Masuda et al. | 424/76 |
| 4,078,050 | 3/1978 | Hart | 424/76 |
| 4,078,055 | 3/1978 | Naganuma et al. | 424/76 |
| 4,154,817 | 5/1979 | Tsuchiya et al. | 424/76 |
| 4,202,882 | 5/1980 | Schwartz | 424/76 |
| 4,256,728 | 3/1981 | Nishino et al. | 422/4 |
| 4,491,563 | 1/1985 | Reusser et al. | 422/5 |
| 4,594,239 | 6/1986 | Pluim | 424/10 |

FOREIGN PATENT DOCUMENTS

| 638266 | 3/1962 | Canada . |
| 761362 | 6/1967 | Canada . |
| 820857 | 8/1969 | Canada . |
| 0031424 | 3/1981 | Japan . |

Primary Examiner—Dennis Albrecht
Assistant Examiner—K. Markowski
Attorney, Agent, or Firm—Saidman, Sterne, Kessler & Goldstein

[57] ABSTRACT

A composition for the removal of odors of a skunk spray is disclosed composed of a shampoo base and an effective amount of a sulfur oxidizing reagent.

9 Claims, No Drawings

SKUNK ODOR SHAMPOO

The present invention relates to a composition and method to chemically destroy the odouriferous principles of skunk spray.

Many pets, particularly dogs, often encounter skunks and are subsequently sprayed by the skunk. In addition many people also encounter skunks in the woods and if not alert may be sprayed by the skunk which subsequently may require a complete cleaning if not disposal of clothes worn at the time. Remedies such as washing or bathing in tomato juice acts to at least partially alleviate the odour problem, however, the skunk odour is persistent and may be noticeable particularly in damp weather especially in the fur and hair of animals which have been sprayed.

There is a need to provide a means to completely eliminate the foul odour derived from skunk spray. By the present invention the active ingredient to remove the odour is most conveniently applied as a dilute solution in a shampoo. Pets which have been sprayed by a skunk are effectively deodourized by a simple shampooing. Furniture, rugs, any upholstery etc. may also be readily deodourized by washing the article with the shampoo containing the active ingredient.

The pungent odour of skunk spray is due to organic sulfur compounds. Dicrotyl sulfide and butyl mercaptan are the main components of skunk spray secretion. Both of these compounds contain divalent (or reduced) sulfur which is the chemical moiety responsible for their odour. A fundamental chemical property of divalent organosulfur compounds is that they are readily oxidized to sulfoxides, sulphones and sulphates. Such oxidized organosulphur compounds differ from the parent divalent compounds in two useful and important ways. Firstly, they are odourless and secondly they are water soluble. Application of this fundamental oxidative process forms the basis of the present concept by the use of a mild oxidizing reagent dissolved in a shampoo base. When a pet which has been sprayed by a skunk is washed with the shampoo containing the reagent, the reagent reacts very rapidly with the sulfur compounds converting them irreversibly to their corresponding oxides. When the pet is subsequently rinsed the converted oxides which are now odourless are washed away.

It is an object of the present invention to provide a composition of matter which is useful for removing the odourous principles of skunk spray.

It is a further object of the present invention to provide a method for the removal of the odourous principles of skunk spray.

These and other aspects may readily be obtained by applying to the area which has been sprayed by a skunk a blend of a shampoo and an effective amount of an aqueous solution of a sulfur oxidizing reagent.

To assess the present concept, test were carried out by first placing a small amount of synthetic butyl mercaptan and diallyl sulphide on a wad of dog hair in a beaker. The hair was then washed with a soap solution containing the oxidizing reagent. Amongst the oxidizing reagents tested was sodium periodate, potassium permanganate, benzoyl peroxide, calcium hypochlorite, hydrogen peroxide, potassium iodate, sodium iodate, potassium bromate, lithium iodate and magnesium iodate. It was noted that all of the reagents tested were effective although did show varying degrees of effectiveness at destroying skunk odour. The effectiveness was assessed by smell.

While all of the reagents tested were more or less effective the iodate ion was found to be preferred. All soluble iodate salts which are acceptable from the veterinary point of view were found to be equally effective (e.g. potassium, sodium, lithium and magnesium iodate). The main difference between the salts is their solubility in the soap solution or shampoo. It was observed that salts with lower solubility, such as potassium iodate at 4.7 g/100 ml in water at 0° C., are more likely to crystallize out of the shampoo in prolonged cold storage than are salts with higher solubility such as lithium iodate at 80.3 g/100 ml in water at 18° C.

The active ingredient, the oxidizing reagent, may be incorporated in a wide variety of shampoos. For example, formulations have been tested made up from industrial shampoo bases such as Cedepon SB-1 TM and Cedepon BS-F TM (both being Trademarks of Domtar, Inc.). Equally successful formulations for test purposes have been prepared by dissolving the iodate salt, about 1 to 5 grams in a small amount of hot water and mixing the resulting solution into a commercially available shampoo such as Life Brand Balsam TM and Protein II Shampoo, TM K Mart Baby Shampoo TM and Shoppers Drug Mart Baby Shampoo. TM While all of the reagents tested were more or less effective in destroying skunk odour, potassium iodate was clearly the most effective. Odour removed by the iodate was instantaneous even when used at concentrations as low as one percent. A three percent solution of potassium iodate in shampoo was found to be stable for several months. Potassium iodate is a stable crystalline salt which dissolves readily in water or in shampoo bases. It appears to have no negative dermatological or toxicological properties and is safe to use.

Obviously, the product is for external use only. Since the product can only function if it contacts the skunk secretion, all affected areas of the pet must be lathered. The product should be kept out of the eyes of the pet.

A shampoo concentrate is mixed with an aqueous solution of an iodate salt such as potassium iodate. Perfume and a colour dye may be added as desired and the pH adjusted to 6–7. A chloride salt, particularly lithium chloride is added as a thickener and to help keep the iodate salt in solution.

EXAMPLE

A shampoo composition for removal of odourous principles of skunk spray is as follows:
- 69 parts water
- 31 parts Cedepon SB-1 TM
- 2% potassium iodate
- 1% lithium chloride
- 0.5% fragrance
- 0.005% dye The skunk shampoo composition was tested by a professional veterinarian and with the assistance of the Research and Productivity Council of Fredericton, New Brunswick, Canada. The prepared product shampoo was used on several freshly skunk-sprayed dogs and on a dog which had a lingering odour from a past encounter. In all cases, the shampoo after use completely removed the skunk odour. The veterinarian commented that he had previously tried a number of products on the market for the same purposes but none was as effective as the present shampoo composition in removing the skunk odour.

The shampoo also underwent a limited test marketing in the spring of 1987. It was provided in one liter bottles to the pet care industry namely, pet stores, veterinarians. The response was very positive with packaging being the only criticism. The pet industry would prefer to buy small containers of the shampoo for resale to their customers.

The principles and modes of preparation and operation of the present invention have been described in the foregoing specification. The invention which is intended to be protected herein, however, is not to be construed as limited to the particular forms disclosed as these are to be regarded as illustrative rather than restrictive. Variations and changes may be made by those skilled in the art without departing from the spirit of the invention.

The embodiments of the invention in which an exclusive property or privilege is claimed are defined as follows:

1. A composition for removal of odourous principles of skunk spray comprising a mixture of shampoo concentrate, sufficient water to dilute such concentrate for use as a shampoo, and a water-soluble iodate salt in the amount of about 1 to 5% by weight of the composition.

2. The composition of claim 1 wherein the iodate salt is selected from the group consisting of: potassium, sodium, lithium, and magnesium iodate.

3. The composition of claim 1, wherein the composition is thickened by the addition of about 2% by weight of lithium salt.

4. The composition of claim 3, wherein the lithium salt is lithium chloride.

5. The composition of claim 1, which additionally includes fragrance.

6. A composition as in claim 1 in which the water-soluble iodate salt is present in the amount of about 1% by weight.

7. A composition for removal of odorous principles of skunk spray comprising a blend of about 31 parts of a shampoo base and 69 parts of a three percent aqueous solution of potassium iodate.

8. The composition of claim 7, wherein the composition is thickened by the addition of about 0.5% to 1.5% lithium chloride salt by weight.

9. A method for the removal of odorous principles of skunk spray, which comprises shampooing the affected area with the composition of claim 1.

* * * * *